(12) United States Patent  
Moireau et al.

(10) Patent No.: US 8,318,264 B2
(45) Date of Patent: Nov. 27, 2012

(54) PROCESS FOR FUNCTIONALIZING A GLASS REINFORCEMENT FOR COMPOSITE MATERIAL

(75) Inventors: Patrick Moireau, Curienne (FR); Maxime Duran, Cavanac (FR); Jean-Baptiste Denis, Paris (FR)

(73) Assignee: Saint-Gobain Adfors, Chambery (FR)

( * ) Notice: Subject to any disclaimer, the term of this patent is extended or adjusted under 35 U.S.C. 154(b) by 886 days.

(21) Appl. No.: 12/294,956

(22) PCT Filed: Mar. 30, 2007

(86) PCT No.: PCT/FR2007/051044
§ 371 (c)(1),
(2), (4) Date: Sep. 29, 2008

(87) PCT Pub. No.: WO2007/113444
PCT Pub. Date: Oct. 11, 2007

(65) Prior Publication Data
US 2011/0076500 A1 Mar. 31, 2011

(30) Foreign Application Priority Data
Mar. 31, 2006 (FR) ..................................... 06 51157

(51) Int. Cl.
*B05D 3/00* (2006.01)
*B05D 3/02* (2006.01)
*H05H 1/00* (2006.01)
*C23C 14/02* (2006.01)
*B32B 17/00* (2006.01)

(52) U.S. Cl. ........ 427/532; 427/533; 427/534; 427/535; 427/536; 427/538; 427/539; 427/385.5; 427/388.4; 427/407.2; 427/407.1; 427/407.3; 428/410; 428/426

(58) Field of Classification Search .......... 427/532–536, 427/538–539, 384, 407.1, 443.2, 428.01
See application file for complete search history.

(56) References Cited

U.S. PATENT DOCUMENTS

| 5,585,147 | A | 12/1996 | Ogawa et al. ................. 427/535 |
| 6,106,653 | A | 8/2000 | Polizzotti et al. .......... 156/379.6 |
| 2001/0054435 | A1* | 12/2001 | Nagao et al. ................... 136/251 |
| 2004/0265505 | A1 | 12/2004 | Winther-Jensen ............ 427/488 |
| 2007/0148463 | A1 | 6/2007 | Winther-Jensen ............ 428/408 |

FOREIGN PATENT DOCUMENTS

| GB | 1 355 769 | 6/1974 |
| GB | 2 290 729 | 1/1996 |
| JP | 58 156546 | 9/1983 |
| JP | 62 111493 | 5/1987 |
| JP | 64 001733 | 1/1989 |
| WO | 99 50199 | 10/1999 |
| WO | 01 85635 | 11/2001 |

* cited by examiner

*Primary Examiner* — Camie Thompson
(74) *Attorney, Agent, or Firm* — Oblon, Spivak, McClelland, Maier & Neustadt, L.L.P.

(57) ABSTRACT

Process for surface functionalization of a glass reinforcement, characterized in that the said reinforcements are chemically modified by means of surface treatment by the action of a homogeneous plasma at atmospheric or sub-atmospheric pressure in a controlled, oxidizing or nitriding gas atmosphere, and in that the said surface portion is contacted with an aqueous impregnating solution of an organic or inorganic matrix, or directly with the matrix.

19 Claims, 3 Drawing Sheets

PROCESS FOR FUNCTIONALIZING A GLASS REINFORCEMENT FOR COMPOSITE MATERIAL

The present invention relates to a process for obtaining composites, which includes a step of impregnating glass reinforcements with an organic or mineral matrix, it not mattering whether said reinforcements are in the form of a roving, a scrim, a woven, a nonwoven, etc.

It is known that the properties of composites essentially depend on the quality of the interface, and in particular the adhesion, between the glass substrate and the organic matrix. Composites are produced at the present time from one or more constituents according to various basic processes, within which dry processes, involving extrusion, are distinguished from wet processes, involving impregnation.

The "glass substrate" is in particular understood, within the context of the present description, but not exhaustively, to mean glass wovens, nonwovens of complex type, veils, mats, glass scrims, especially for a building application.

A typical sequence of steps for a wet process comprises the suspending, in an aqueous solvent, of the constituent polymer of the matrix and of the glass substrate or reinforcement, a vacuum filtration and an operation of forming the product, for example by calendering. The residual water is then removed in an oven. Thus, in the case in which the manufacture of the composite is carried out by a wet process, the quality of the impregnation (speed, uniformity of the coating, etc.) is a factor of paramount importance for the choice of the most effective process. This factor determines in particular the performance of the composites finally obtained and the customer's satisfaction that results therefrom.

Furthermore, any visible impregnation defect, even one that is minimal and does not affect the overall performance of the composite, may give an a priori unfavorable aspect to the product.

Another key factor is of course the economic cost of these processes when they are developed on an industrial scale.

Very many publications are known in the literature relating to the manufacture of composites and more particularly to impregnation problems with reinforcing fibers. Thus, it is now known that it is in particular possible to vary various factors in order to improve the impregnation, for example:
- on the structure of the reinforcement, by modifying the porosity of the material or the orientation of the fibers;
- on the chemistry of the size or of the binders, by modifying the surface tension of the fibers, the swelling of the size, the surface roughness, the redissolving of chemical species, etc.;
- on the chemistry of the resins, suspensions or emulsions for impregnating the fibrous material, for example by modifying the surface tension of the liquid or its rheology; and
- on the process parameters, by modifying the impregnation time, the pressure, the temperature, the degree of dilution, etc.

However, lack of adhesion between the glass reinforcement and the organic matrix is essentially the result of poor wettability of the sized fiber constituting the reinforcement by the impregnation solution. The lack of adhesion may thus be directly due to the chemical reactivity of the surface of the glass reinforcement by the solution used.

It is known that glass reinforcements for composites, whether in the form of rovings, scrims, wovens, nonwovens or the like, require, in order to manufacture them, more particularly the fiberization of the constituent glass fibers, the use of complex organic compositions. These compositions provide both the bonding between the glass filaments in the fiber and between the reinforcement and the matrix, and act as lubricant and protect the filaments from mutual abrasion.

Organic compositions playing such a role are in general termed in the art "sizes" or "sizing compositions".

It is generally accepted that the impregnation problems encountered between glass reinforcements and the organic matrix result from poor compatibility between the size coating the reinforcements and the solution used for carrying out said impregnation.

Certain solutions reported in the prior art for improving impregnation techniques, especially in the field of textiles for electronic applications or for high-performance material applications, recommend a step of removing the size present on the reinforcements and a treatment step with the aim of depositing, in place of the size, an organic compound known in the art as a "coupling agent". The role of this coupling agent is to improve the adhesion between the glass reinforcement and the organic matrix. As an example of coupling agents most commonly used, mention may be made of organosilanes.

According to a first example, the step of removing the size may be carried out by a heat treatment on the glass reinforcement at a temperature of about 400° C. for a few hours, or even for a few tens of hours. Indeed, it has been observed that the treatment has to be extended until the size has been completely removed, the persistence of even a very small amount of size resulting in a very considerable reduction in the adhesion between the reinforcement and the matrix in the composite product. This treatment thus has major drawbacks owing to its very low productivity and its energy cost.

Alternatively, U.S. Pat. No. 5,585,147 discloses a process for the surface treatment of a glass fabric in which the size is completely removed by an atmospheric-pressure plasma of a gas preheated to a temperature between 100° C. and 500° C., prior to a step of bringing it into contact with a coupling agent consisting of an organosilane.

According to another known method, the glass reinforcement may be treated by means of a filamentary electrical discharge in air at atmospheric pressure, of the corona type.

Such treatments are well known, in particular from patent application EP 1 044 939 A1 relating to the surface treatment of reinforcing fibers or from the application JP 2-166129 relating to a glass fabric base.

A surface treatment carried out using a corona electrical discharge is characterized by an electrical discharge regime of the filamentary type at atmospheric pressure in air.

Specifically, in most industrial gases (argon, air, nitrogen, etc.), their breakdown at atmospheric pressure, which is in fact a transition to a conducting regime of the gas, is initiated by a large number of independent filaments or microdischarges, the characteristics of which are in particular a lifetime shorter than $10^{-9}$ s, a mean radius of less than 100 μm and a current density between 100 and 1000 A/cm$^2$. The microdischarges are initiated and extinguished randomly over the entire surface of the electrodes, at least one of which electrodes may be covered with a dielectric barrier. In this filamentary regime, the materials to be treated are in direct contact with the electrical discharge, that is to say are between the two electrodes (in situ treatment), the surface treatment of the materials generally taking place more or less homogeneously. In contrast, locally, the transformations induced by this type of treatment with filamentary discharges are highly heterogeneous. Thus, one surface portion of the material having undergone a series of microdischarges will be much more modified, or even in extreme cases etched and degraded, than another portion that has not been subjected thereto, even on inorganic bases such as glass. Furthermore, corona electrical discharges, owing to their intensity, tend to create, in the zones where the microfilaments strike the surface of the reinforcement, regions of weakness (local heating, preferential crack initiation) which reduce the mechanical properties of the final composite product.

Furthermore, it has been demonstrated that the consequences of the corona treatment on the surface portion of the substrate cannot in general persist over time.

Filamentary corona electrical discharges, although providing effective treatment of the surface of a reinforcement, also show other major drawbacks:

- the treatment is often limited to the treatment of 2D (two-dimensional) structures, the plane-plane configuration of the electrodes being adapted to a 2D geometry, the fabrics pass through the discharge, and they may be treated on their faces;
- the filamentary treatment is not homogeneous and is not easily controllable, knowing that its effectiveness depends greatly on the relative humidity of the air, for example;
- the filamentary treatment may degrade, by local heating or by fracture initiation, the treated surface and lead to a loss of mechanical properties of the fiber;
- the filamentary treatment may deposit a large amount of electrical charge on the surface of the reinforcement, which can then disturb the subsequent impregnation step; and
- the chemistry of the treatment is limited to the oxidation of the substrates.

The object of the present invention is to provide a novel process for obtaining a composite, which in particular includes a step of treating the glass substrate before its impregnation, the process being simpler and more economic than those described above.

More precisely, the invention relates to a process for obtaining a composite comprising a glass reinforcement or substrate in an organic or mineral matrix, said reinforcement or substrate being in the form of a roving, a scrim, a veil, a woven, a nonwoven or the like, comprising at least the following steps:

- surface treatment of the glass reinforcement with a homogeneous plasma of a gas mixture, in a controlled gaseous atmosphere, for oxidation or nitriding of the organic size present on the surface of the glass reinforcement; and
- impregnation of the functionalized reinforcement with said nitriding or said oxidation with an aqueous emulsion or suspension of the matrix or directly with the matrix.

The homogeneous plasma is generally employed at a pressure below atmospheric pressure, for example of the order of $10^{-5}$ bar and preferably employed substantially at atmospheric pressure.

Preferably, the temperature of the gas mixture is below 90° C.

For example, the gas mixture may comprise or consist of oxygen.

According to another embodiment, the gas mixture comprises or consists of $N_2$ or a mixture of $N_2$ and a reducing gas of the $H_2$ or $NH_3$ type, or else comprises or consists of $NH_3$.

The invention also relates to the glass substrate surface-treated with a homogeneous plasma as described above and to a composite that can be obtained by the process as described above.

In the composite according to the invention, the organic matrix is chosen from the group formed by thermoplastic matrices and thermosetting matrices, for example from the group formed by polyvinyl alcohol, polyvinyl acetate, polyvinyl chloride, polytetrafluoroethylene and copolymers derived from these polymers, such as ethylene/vinyl acetate copolymers.

In the composite according to the invention, the glass reinforcement is preferably chosen from glass wovens, nonwovens of complex type, veils, mats, glass scrims, especially for a building application, unitary strands sized or converted beforehand, and compound strands, it being possible for the type of glass to be chosen from E-glass, R-glass, ECR-glass and S-glass, or else any glass composition known for its corrosion-resistance properties under acid or basic conditions and/or for its high mechanical strength.

The present process may be carried out in various ways, two examples of which are given below:

According to a first method of implementation, the following succession of steps is carried out:
1. manufacture of a reinforcement (e.g. roving, scrim, woven, nonwoven) with size;
2. preparation of the surface by a plasma treatment as described above; and
3. impregnation of the treated reinforcement.

According to another method of implementation, the following succession of steps is carried out:
1. manufacture of the elementary reinforcements (e.g. rovings);
2. preparation of the surface of the elementary reinforcements by the plasma treatment according to the invention;
3. manufacture of the complex reinforcement from the treated elementary reinforcements (for example in the form of wovens, nonwovens, veils, scrims); and
4. impregnation in an organic matrix.

According to this method, steps 3 and 4 may be reversed. In the latter case, it will be preferable to provide a fifth step of bonding by calendering, so as to further improve the adhesion.

Of course, the invention could be carried out using other methods easily accessible to those skilled in the art, which would be burdensome if all were reported in the present description. All possible methods of implementing the present process thus fall within the scope of the present invention.

From a technical standpoint, the homogeneous plasma electrical discharge according to the invention is initiated between two electrodes subjected to an appropriate potential difference in a controlled atmosphere of a chosen gas mixture. Upon applying the electric field, the gas ionizes (avalanche principle). The electrons and ions created are accelerated and interact with the neutral particles of the gas. Depending on their kinetic energy, this results in the creation of new ionized particles and chemical species in an excited state.

The active species created within an ionized gas are in principle electrons, positive and negative ions, metastable atoms and molecules, the species having kinetic or vibrational energy, free radicals and photons. All these species are capable of interacting with the surface of the materials. Their action can vary depending on the type of electrical discharge and on the experimental conditions that determine, in particular, their number, their distribution and their energy.

In the case of a surface treatment according to the invention, the energy distribution of the electrons is centered on a few electron volts, typically between 0.5 and 100 eV. The abovementioned species come into contact with the surface of the reinforcement to be treated, i.e. mainly with the organic size used to fiberize the reinforcement. Each species is capable of chemically modifying the size to a greater or lesser depth depending on its energy and on its mean free path in the solid.

Without this being able to be understood as or tied to any theory, the surprising effects observed by the Applicant on the rate and/or quality of impregnation of the reinforcements treated according to the invention could be explained by a surface activation of the reinforcements, due to various structural changes such as crosslinking or functionalization (in particular by the grafting of new chemical functional groups) of the substrate, or even in modification of the roughness, physico-chemical state, electrical charge or mechanical state (density, crosslinking) of the treated organic surfaces.

The present process has the following advantages:
- the process for functionalizing the surface of the reinforcement is carried out without the assistance of solvents;
- the configuration of the homogeneous plasma treatment may be directly adapted in line with the method of manufacturing the coated reinforcements;
- the plasma treatment may be carried out at atmospheric pressure;
- the plasma treatment is homogeneous irrespective of the shape and the dimensions (2D, 3D) of the reinforcement to be treated;
- the plasma treatment according to the invention does not impair the mechanical properties of the reinforcements;
- the surface chemistry of the plasma treatment can be modulated, in particular depending on the nature of the size and of the organic matrix;
- the surface charge is less, in particular with 3D treatments the postdischarge (remote plasma) method illustrated by FIG. 2; and
- the plasma treatment according to the invention limits the ageing problems of the treated reinforcement observed previously in the case of reinforcements treated by corona electrical discharges.

Among the many possible variants characterizing the plasma treatment according to the invention, mention may be made of:
- plasma treatment using magnetron cathode sputtering and/or IB (ion beam) sputtering;
- plasma grafting of all known functional groups based on oxygen or nitrogen; and
- plasma-enhanced deposition of chemical species of the oxide or nitride type, in particular $SiO_xC_y$, $SiO_xN_yC_z$, $AlO_x$, $TiO_x$, $TiN_x$ and mixtures thereof.

The sizes that can be surface-modified by the present process are for example the sizes for bulk composites, such as those used in automotive applications, having to provide very strong bonding with the organic matrix are for the purpose of obtaining very high mechanical properties (epoxy composite, certain high-temperature PA-type thermoplastics) or ageing properties by providing chemical bonds that are less sensitive to hydrolytic reactions (applications in a wet or corrosive medium). The compositions of these sizes are most particularly mixtures of emulsions based on various polymers (epoxy, polyester, polyurethane, polyvinyl acetate, etc.) combined with coupling agents (silanes, etc.) and processing aids (lubricants, surfactants, etc.).

The emulsions or suspensions that can be used according to the present invention are for example aqueous solutions of PVA, PVC, SBR, acrylic, PTFE, silicone, etc.

According to the invention it is possible to use as reinforcement open products of the wide-mesh nonwoven or scrim type (called laid scrims) intended for building applications (wall cladding), for the reinforcement of paper, for protective clothing, for phenolic grafting (grinding wheels).

The coating on the treated reinforcement may be deposited using any known impregnation method, among which the processes are called roll coating, dip coating and spray coating.

Depending on the method of impregnation used, the base products may also be of the closed woven fabric type, chopped (thermoplastic, automotive) strands or veils or mats, or products intended for filament winding applications (tanks, pipes, etc.).

The potential applications of the present invention are numerous. In fact, the glass fibers, whether or not converted into the form of finished products, are intended for mainly reinforcing polymeric organic matrices. In all cases, the compatibility and the quality of the impregnation by the matrix to be reinforced are two key factors that have a very considerable influence on the mechanical properties and the durability of the composite obtained.

The many potential applications may include, although not exhaustively:
1. Composites requiring impregnation by an organic matrix in order to manufacture "bulk" composites. These are plane (2D)-type or volume (3D)-type composites such as composites reinforced by wovens, complexes or nonwovens, such as veils, mainly based on polyester or epoxy resins. Processes such as the infusion techniques may have the great advantage of improving the impregnation and in particular the rate of wetting of the reinforcement. The main fields of use are in transport vehicles, sports and leisure articles, buildings (reinforced pipes, certain cladding panels, etc.), civil engineering components (roadway or pedestrian bridges, mats, structural elements, etc.);
2. SMC/BMC systems reinforced with long chopped strands or products of the Unifilo® mat type may also be relevant. Impregnation in the form of a paste by the matrix is also a key point both for the final appearance of the product and for the mechanical properties. The applications are mainly in the transport field, but quite a number of other applications exist in electrical systems, sanitary equipment, etc;
3. Woven or nonwoven products intended for the reinforcement of particular matrices and for surface properties that are barely compatible with good adhesion to glass substrates, even those pretreated with a size. This particularly relates to matrices such as PVC, PTFE and any copolymer derived from these two polymers. The applications are diverse, including conveyor belts for the agri-food industry, protection against chemical attack (NBC military equipment made of PTFE), stadium covers, etc.; and
4. Woven or nonwoven glass scrims having two different levels to their manufacturing process and their use:
on as-produced scrims, the surface modification of the filaments and more particularly modification in the properties of the size covering them, may allow better impregnation to the core and better adhesion between the matrix and the glass filaments (improved interface). This is particular important for applications requiring good resistance to alkaline attack such as for applications in the façade cladding field, or cement or plaster panel joints, cement board, or applications requiring good moisture resistance, such as roofing or insect screen applications, etc. On scrims already coated with a coating, the surface modification may allow better compatibility or adhesion with the products to be reinforced, especially in building applications (cements often modified by polymers such as acrylics) or applications in the paper field (reinforced papers, wiping paper, etc.).

These examples represent a few processes and applications among the main fields and markets for glass fiber reinforcement. The applications and processes are very numerous and it is impossible to mention them all within the context of the present description. Nevertheless, this plasma technology for surface modification has the advantage of being very flexible and having a great variety as regards types of treatment that can be applied which consequently can be applied to a large part of reinforcing products, in particular the products that have already undergone a first conversion step, such as a woven, a scrim, a mat, etc.

Other features and advantages of the invention will become apparent over the course of the following non-limiting description of various embodiments of the invention, illustrated by FIGS. 1 to 4 in which.

The glass-based reinforcement material 1 is directed into a surface treatment zone in an installation generating a homogeneous plasma suitable for implementing the process. This installation, illustrated schematically by FIG. 1, is of a known type.

Figure 1:
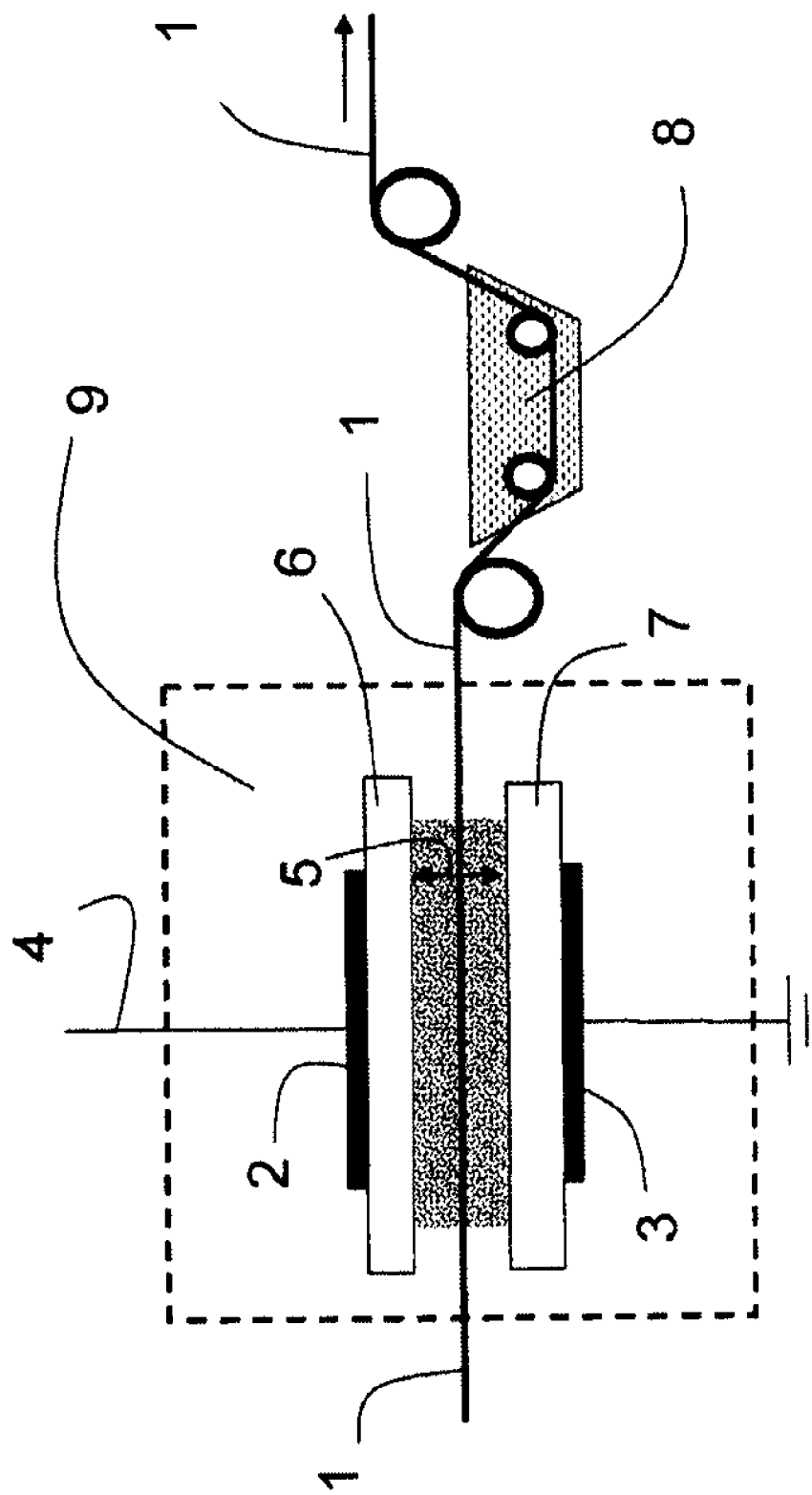
FIG. 1 is a schematic view of an installation for implementing the surface treatment process according to the invention.

When the controlled gas atmosphere is at low pressure, the installation includes a chamber represented by the reference 9 in FIG. 1. The chamber 9 is sealed from the external environment and can thus be the site of an atmosphere that is controlled in terms of composition and pressure. For this purpose, it has a plurality of pipes intended for delivering and discharging said atmosphere (these not being shown in FIG. 1).

The plasma device comprises two electrodes 2 and 3 connected to the tunnels of a variable-frequency voltage generator 4. The electrodes positioned facing each other define between them a suitable treatment volume 5 for passage of the glass reinforcement 1, which may equally well be in the form of a roving, a scrim, a woven, a nonwoven or the like.

According to another feature of the installation when the controlled gas atmosphere is at atmosphere pressure, the chamber 9 is optional, but each of the electrodes 2, 3 is coated with a dielectric layer 6, 7 directed toward the treatment volume 5. In the exemplary embodiment shown in FIG. 1, each dielectric layer 6, 7 is for example based on alumina and separated by a thickness of between 0.1 and 20 mm, preferably between 1 and 6 mm.

According to the embodiment of the invention in which the controlled atmosphere consists of an oxidizing or nitriding gas at low pressure, typically of the order of $10^{-5}$ bar. In the embodiment in which an atmospheric-pressure plasma is used, the gas consists predominantly of nitrogen, by itself or mixed with reducing species ($NH_3$, $H_2$, etc.) or of an inert gas of the helium or argon type, mixed with one or more oxidizing species (especially those obtained by ionizing $O_2$, $CO_2$, $H_2O$, etc.).

By applying a suitable voltage across the terminals of the electrodes 2, 3 in this case here an AC voltage of the order of a few kV and at a frequency varying from 1 kHz to a few tens of MHz, in the presence of said controlled atmosphere, a homogenous electrical discharge is initiated.

Figure 3:
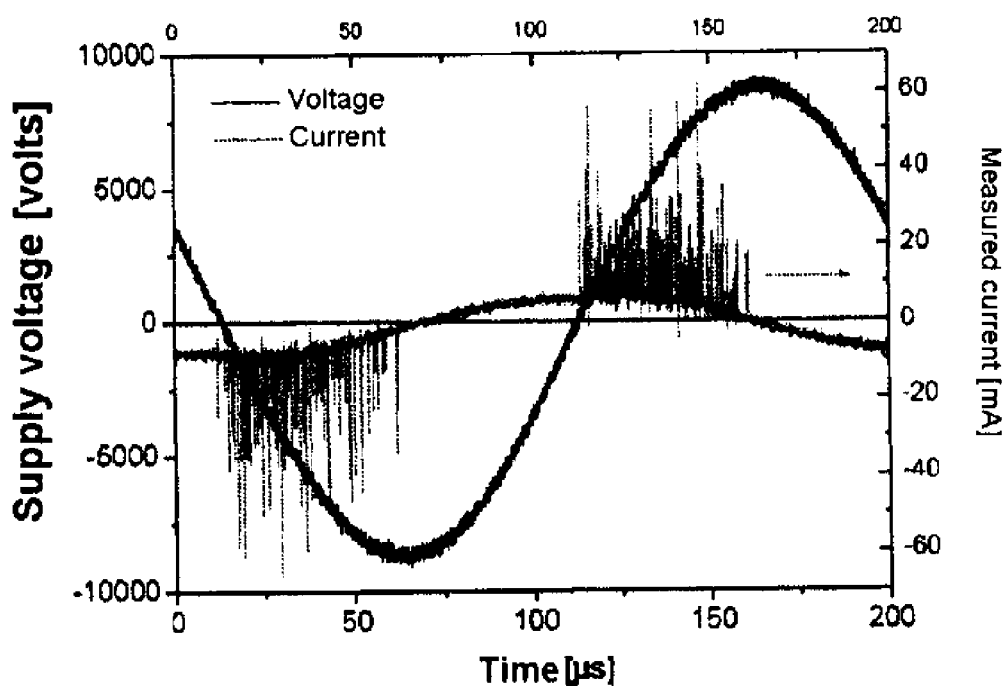
FIG. 3 is an oscillogram of a filamentary regime.

It will be recalled that, within the context of the invention, and more generally, a discharge is said to be homogeneous, as opposed to a corona discharge, when it is not possible, on a macroscopic and microscopic scale, to perceive, between the electrodes, the presence of an arc or filaments or microdischarges, between two electrodes subjected to a potential difference in a controlled atmosphere of a gas mixture, as defined above, and at atmospheric pressure. The nature of the regime may be demonstrated by a voltage/current oscillogram (cf. FIGS. 3 and 4). According to the invention, the presence of a confined homogeneous discharge between the electrodes 6 and 7, in the treatment zone 5, in an oxidizing or nitriding plasma atmosphere, advantageously makes it possible for the surface of the sized glass reinforcement to be chemically activated, in particular enabling it to be prepared for the impregnation step, illustrated schematically by the immersion of the treated reinforcement in a bath 8 of an aqueous solution of an emulsion or suspension of the organic matrix. Without departing from the scope of the invention, the glass reinforcement may also be impregnated by direct immersion in the matrix, that is to say without an intermediate step such as the deposition of a coupling agent.

Figure 4:
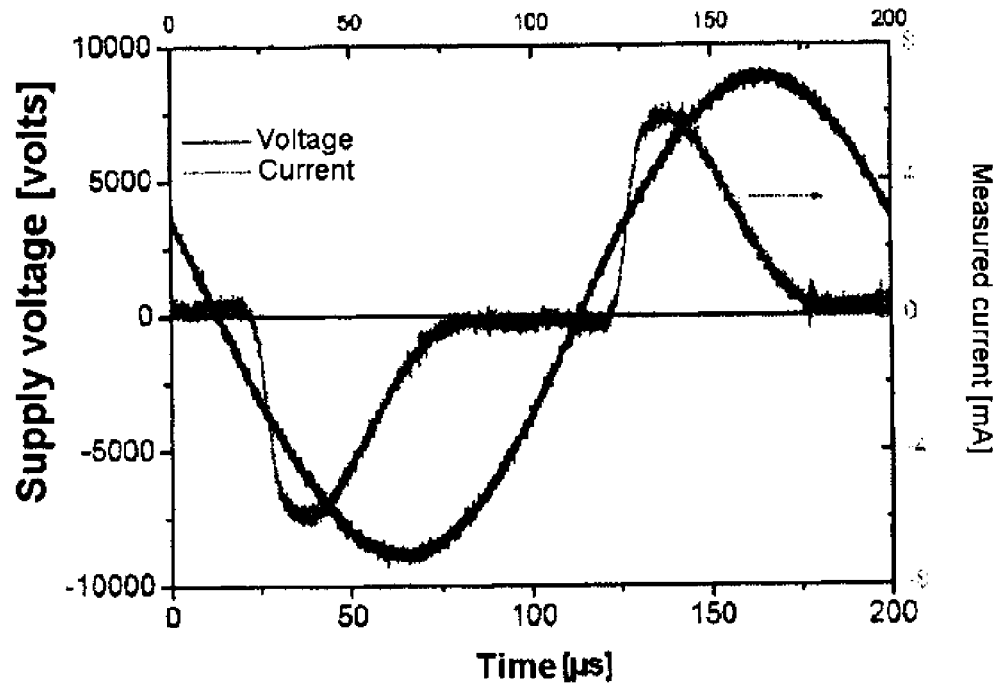
FIG. 4 is an oscillogram of a discharge in homogeneous regime.

According to another possible embodiment for implementing the process according to the invention and illustrated by FIG. 4, a device 10 is used that generates a homogenous remote or blown plasma, which is itself injected and fills a housing 11 of suitable cross section, through which the reinforcement in its various possible forms runs and undergoes the treatment of functionalizing its surface.

The surface portions of these fibers, the surface of which has been chemically activated by the functionalized treatment according to the invention, are then impregnated with an aqueous solution 8 comprising the organic matrix, in emulsion or suspension form.

The advantages of the present invention are illustrated by the following nonlimiting examples of the present description.

EXAMPLE 1

In this example, the influence of a homogenous plasma treatment according to the present invention on a glass woven used for reinforcement in a composite was measured. The woven was formed from a 9 μm/68 tex/Z20 base strand. The woven, with a density of 209 g/m$^2$ comprised 173/10 cm warp strands and 126/10 cm weft strands. The size used was a conventional size of the starch-based textile type, mixed with lubricants.

The glass woven was subjected to a homogenous plasma treatment in a plasma reactor comprising a vacuum chamber that included two flat metal electrodes connected to a radiofrequency generator (capacitively coupled reactor with parallel electrodes). The air contained in the chamber was sucked out by a turbomolecular pump coupled to a rotary pump so as to obtain a final pressure of around 5·10$^{-5}$ bar. The substrate to be treated was placed on the bottom electrode. The plasma gas was injected into the reactor by means of a mass flow rate regulator. The substrate was maintained at ambient temperature (about 21° C.). The plasma was formed by applying an rf potential at 13.56 MHz to the driving electrode.

The gas used was either oxygen at a pressure of 60 mTorr (i.e. about 8 pascals) or $NH_3$ at a pressure of 150 mTorr (i.e. about 20 Pa). When the gas was oxygen, the driving electrode was supplied with 280 watts of power. When the gas was $NH_3$, the driving electrode was supplied with 190 watts of power. The duration of the plasma treatment was in all cases 5 minutes.

The reinforcements thus obtained were subjected to a tensile strength test according to the NF-EN-ISO 13934-standard, measuring the tensile properties of the wovens by the strip method (determination of the maximum force and the maximum elongation of the woven).

The results obtained are given in Table 1:

TABLE 1

|  | Tensile strength (newtons) |
|---|---|
| Reference (no treatment) | 990 ± 40 |
| $O_2$ plasma treatment | 1075 ± 90 |
| $NH_3$ plasma treatment | 1050 ± 90 |

Comparison of the results shows that the plasma treatment does not impair the mechanical properties of the reinforcement and consequently those of the final composite obtained after impregnation in the organic matrix.

EXAMPLE 2

Various glass wovens of the same type as those of Example 1 were subjected to an oxidizing or reducing plasma treatment identical to that described in Example 1, and the chemical composition of the surface layer was measured by XPS over a thickness of 5 nm. The compositions obtained may be compared using Table 2 with those of a reinforcing woven that has not undergone surface functionalization plasma treatment according to the invention.

This table shows that the silicon content in the surface layer is substantially identical to that of the untreated woven. Likewise, the carbon content remains very predominant in the surface layer of the treated woven, showing that only the outermost atomic layers of the woven were modified by the plasma treatment.

TABLE 2

|  | Carbon | Nitrogen | Oxygen | Fluorine | Silicon |
|---|---|---|---|---|---|
| Reference (no treatment) | 74 | 1 | 21 | 0 | 4 |
| $O_2$ plasma treatment | 59 | 0.5 | 3 | 1.5 | 8 |
| $NH_3$ plasma treatment | 70 | 8 | 17.5 | 0.5 | 4 |

EXAMPLE 3

The rate of impregnation of a reinforcing woven obtained by homogenous plasma treatment in a reduced oxygen atmosphere in accordance with Example 1 was determined by measuring the time needed for complete penetration of a 3 µl water droplet into the woven, by means of a device comprising a camera linked to a measurement computer. The time needed for complete absorption was 22.5 seconds for the untreated woven, whereas it was 2.4 seconds for the woven pretreated by the homogeneous plasma.

EXAMPLE 4

The impregnation properties, for impregnation with an aqueous PTFE (polytetrafluoroethylene) suspension, of the reinforcing woven treated by the homogenous plasma treatment in a reduced oxygen atmosphere in accordance with Example 1 were determined.

For this purpose, the phenomena associated with capillary impregnation of the glass strands and wovens were measured by means of a Wilhelmy balance for determining the rate of capillary impregnation and the mass of liquid retained by the woven or the strand.

The device of the Wilhelmy balance comprises a precision (0.1 mg) balance under which a fine metal hook connected to the measurement plate can be fixed. This hook is used to suspend a glass fiber roving specimen or a woven specimen.

The specimens were prepared by cutting strips 5 cm in length by 0.5 cm in width from the reinforcing wovens. These specimens were taken from reels of woven that were maintained for 24 hours at 20° C.±3° C. with a residual humidity of 50%±5%.

The strips were firstly suspended from the Wilhelmy balance by means of the hook located underneath. The woven suspended from the balance by means of the hook was then brought into contact with a liquid.

The capillary rise of the liquid into the strand or the woven measured by the balance was recorded as a function of time. When the woven reached liquid saturation, it was removed and its mass recorded. The measured mass corresponds to the sum of the mass of the dry fabric and the mass of the impregnated liquid.

The results were expressed in the form of curves giving the mass of impregnated liquid as a function of the square root of the time. The linear portion of this curve was then used to obtain a slope value k therefrom. This value, expressed in $g/s^{1/2}$, according to Washburn's law, is characteristic of the rate of impregnation of the liquid into the strand or woven. A high k value can then be associated with a rapid capillary impregnation. The mass of retained liquid is also characteristic of the impregnatability or wettability properties, i.e. the chemical compatibility between the reinforcement and the solution.

The results obtained, are given in Table 3, make it possible to observe the very considerable increase in the rate of impregnation of a woven treated according to the present invention.

In particular, the table shows that the mass of retained liquid increases considerably after plasma treatment. This increase is accompanied by a significant increase (by a factor of 6) in the rate of impregnation of the reinforcement in the aqueous solvent.

TABLE 3

|  | k (in $g/s^{1/2}$) | Liquid mass (g) |
|---|---|---|
| Reference (no treatment) | 0.43 | 14.2 |
| $O_2$ plasma treatment | 3.25 | 19.7 |

EXAMPLE 5

Figure 2:
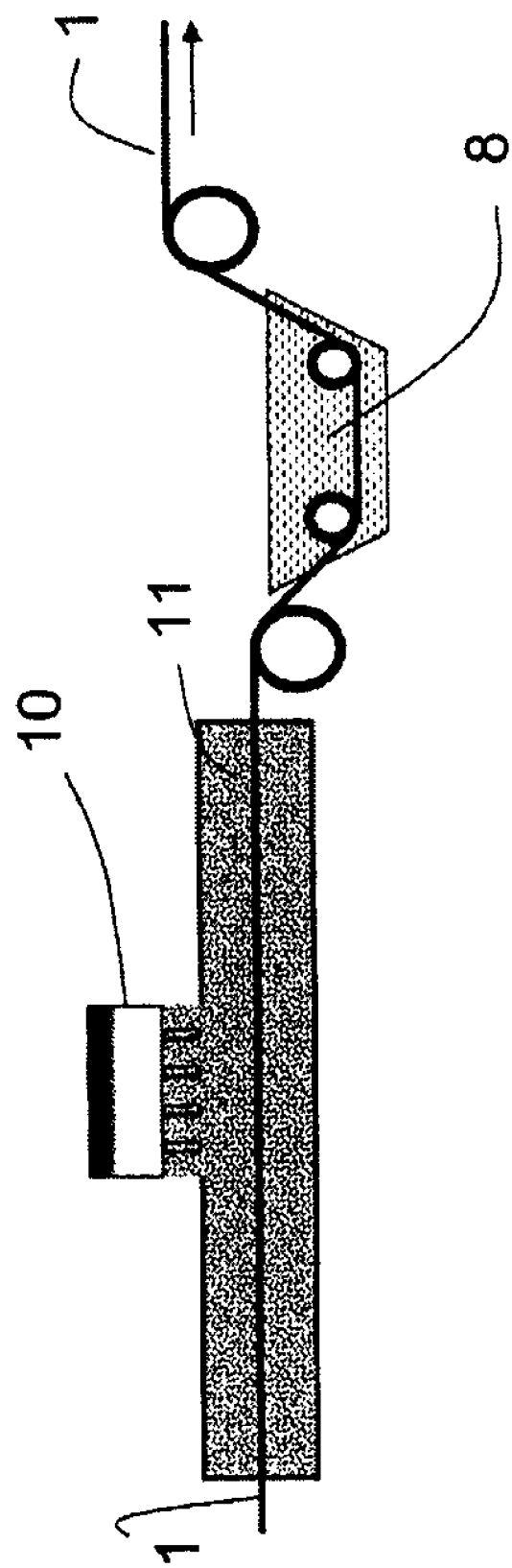
FIG. 2 illustrates the integration of an alternative embodiment comprising the implementation of a remote-plasma installation.

A glass reinforcement roving, made up of a 2400 tex fiber (2000 2.4 µm filaments) and incorporating an epoxy-type size, including amine and methacrylate coupling agents and lubricants of the wax type and an alkylbenzene, was used in this example. Said roving was treated according to the invention by remote-plasma source at atmospheric pressure according to the principles described above in relation to FIG. 2, with a $N_2$ plasma gas. The plasma source used was that sold by Acxys Technologie under the reference UL120.

The glass roving moved through the plasma zone at a rate of 2 meters per minute. The nitrogen was injected into the tube reactor of 1 m length at rate of 250 liters per minute. The Acxys plasma source was activated with a power of 2000 W.

The impregnation capacity of the roving thus treated in an aqueous solvent was determined by immersing the end of the roving in water containing a colored pigment, for comparison with an untreated roving. After two minutes, the colored water rose 14 cm by simple capillary effect into the treated specimen, as opposed to 10 cm in the untreated specimen.

The invention claimed is:

1. A process for obtaining a composite comprising a glass reinforcement or substrate in a matrix, said process comprising:
    treating a surface of the glass reinforcement or substrate having an organic size with a homogeneous plasma of a gas mixture, in a controlled gaseous atmosphere, for oxidation or nitriding of the organic size present on the surface of the glass reinforcement or substrate to obtain a functionalized reinforcement or substrate; and
    impregnating the functionalized reinforcement or substrate with an aqueous emulsion or suspension of the matrix or directly with the matrix.

2. The process as claimed in claim 1, wherein the matrix is selected from the group consisting of thermoplastic matrices and thermosetting matrices.

3. The process as claimed in claim 1, in which the homogeneous plasma is employed at a pressure below atmospheric pressure.

4. The process as claimed in claim 1, in which the homogeneous plasma is employed substantially at atmospheric pressure.

5. The process as claimed in claim 1, in which the temperature of the gas mixture is below 90° C.

6. The process as claimed in claim 1, in which the gas mixture comprises oxygen.

7. The process as claimed in claim 1, in which the gas mixture comprises $N_2$ or a mixture of $N_2$ and a reducing gas of $H_2$ or $NH_3$.

8. The process as claimed in claim 1, in which the gas mixture comprises $NH_3$.

9. A glass reinforcement surface-treated with a homogeneous plasma as claimed in claim 1.

10. A composite obtained by the process as claimed in claim 1.

11. The composite as claimed in claim 10, in which the matrix comprises at least one polymer selected from the group consisting of polyvinyl alcohol, polyvinyl acetate, polyvinyl chloride, polytetrafluoroethylene and a copolymer comprising at least one of these polymers.

12. The composite as claimed in claim 11, in which the copolymer is ethylene/vinyl acetate.

13. The composite as claimed in claim 10, in which the glass reinforcement is at least one selected from the group consisting of a glass woven, a nonwoven of complex type, a veil, a mat, a glass scrim, unitary strands sized or converted beforehand, and compound strands, wherein the type of glass is selected from the group consisting of E-glass, R-glass, ECR-glass and S-glass, and any glass composition known for its corrosion-resistance properties under acid or basic conditions, for its high mechanical strength, or a combination thereof.

14. The composite as claimed in claim 10, in which the matrix comprises an ethylene/vinyl acetate copolymer.

15. The process as claimed in claim 1, in which the homogeneous plasma is employed at a pressure of $5 \times 10^{-5}$ bar, and in which the glass reinforcement or substrate has an organic size present on the surface thereof.

16. The process as claimed in claim 1, in which the gas mixture consists of oxygen.

17. The process as claimed in claim 1, in which the gas mixture consists of $N_2$ or a mixture of $N_2$ and a reducing gas of $H_2$ or $NH_3$.

18. The process as claimed in claim 1, in which the gas mixture consists of $NH_3$.

19. The process as claimed in claim 1, wherein the functionalized reinforcement or substrate is impregnated with an aqueous emulsion or suspension of the matrix.

* * * * *